United States Patent
Ha

(10) Patent No.: US 10,350,091 B2
(45) Date of Patent: Jul. 16, 2019

(54) MOTION ASSISTANCE APPARATUS AND CONTROL METHOD OF THE SAME

(71) Applicant: Samsung Electronics Co., Ltd., Suwon-si, Gyeonggi-do (KR)

(72) Inventor: Taesin Ha, Seongnam-si (KR)

(73) Assignee: Samsung Electionics Co., Ltd., Gyeonggi-do (KR)

( * ) Notice: Subject to any disclaimer, the term of this patent is extended or adjusted under 35 U.S.C. 154(b) by 582 days.

(21) Appl. No.: 15/047,842

(22) Filed: Feb. 19, 2016

(65) Prior Publication Data

US 2017/0065440 A1 Mar. 9, 2017

(30) Foreign Application Priority Data

Sep. 4, 2015 (KR) ........................ 10-2015-0125671

(51) Int. Cl.
*A61H 1/02* (2006.01)
*A61F 2/60* (2006.01)
(Continued)

(52) U.S. Cl.
CPC ........... *A61F 2/605* (2013.01); *A61H 1/0244* (2013.01); *A61H 3/00* (2013.01); *B25J 9/0006* (2013.01); *B25J 13/085* (2013.01); *A61H 2201/0192* (2013.01); *A61H 2201/1215* (2013.01); *A61H 2201/1463* (2013.01);
(Continued)

(58) Field of Classification Search
CPC ......... A61F 2/605; A61H 1/0244; A61H 3/00; A61H 2201/5084; A61H 2201/5079; A61H 2201/5007; A61H 2201/1676; A61H 2201/165; A61H 2201/164; A61H 2201/1628; A61H 2201/1463; A61H 2201/0192; A61H 2201/5061; B25J 13/085; B25J 9/0006
See application file for complete search history.

(56) References Cited

U.S. PATENT DOCUMENTS

| | | | |
|---|---|---|---|
| 7,524,297 B2 | 4/2009 | Shimada et al. | |
| 7,947,004 B2 | 5/2011 | Kazerooni et al. | |

(Continued)

FOREIGN PATENT DOCUMENTS

| | | | |
|---|---|---|---|
| JP | 3917432 B2 | 5/2007 | |
| JP | 4112543 B2 | 7/2008 | |

(Continued)

*Primary Examiner* — Quang D Thanh
(74) *Attorney, Agent, or Firm* — Harness, Dickey & Pierce, P.L.C.

(57) ABSTRACT

Example embodiments relate to a control method of a motion assistance apparatus including a fixing module attached to a user, a driving module fixed to the fixing module to generate rotation power, a supporting module configured to support a portion of a body of the user and driven by the driving module, a force sensor configured to measure a magnitude of force applied to the fixing module, and a controller configured to control the driving module, the method including generating, by the driving module, a driving torque to drive the supporting module, measuring a direction and a magnitude of force indicated by the force sensor, calculating a compensation torque to minimize the measured magnitude of force, and driving the driving module by adding the compensation torque to the driving torque.

16 Claims, 13 Drawing Sheets

(51) Int. Cl.
*B25J 9/00* (2006.01)
*B25J 13/08* (2006.01)
*A61H 3/00* (2006.01)

(52) U.S. Cl.
CPC .. *A61H 2201/164* (2013.01); *A61H 2201/165* (2013.01); *A61H 2201/1628* (2013.01); *A61H 2201/1676* (2013.01); *A61H 2201/5007* (2013.01); *A61H 2201/5061* (2013.01); *A61H 2201/5079* (2013.01); *A61H 2201/5084* (2013.01)

(56) References Cited

U.S. PATENT DOCUMENTS

| | | | |
|---|---|---|---|
| 2006/0052732 A1* | 3/2006 | Shimada | A61F 5/0102 602/5 |
| 2006/0276728 A1* | 12/2006 | Ashihara | A61F 5/0102 601/5 |
| 2008/0161937 A1* | 7/2008 | Sankai | A61H 3/008 623/25 |
| 2009/0292369 A1* | 11/2009 | Kazerooni | B25J 9/0006 623/27 |
| 2010/0324699 A1* | 12/2010 | Herr | A61F 2/66 623/27 |
| 2012/0226203 A1 | 9/2012 | Nakashima et al. | |
| 2013/0331744 A1* | 12/2013 | Kamon | A61H 3/00 601/35 |
| 2015/0127018 A1* | 5/2015 | Lim | A61H 3/00 606/130 |
| 2015/0196403 A1* | 7/2015 | Kim | A61F 2/70 623/24 |
| 2015/0197008 A1* | 7/2015 | Yoon | B25J 9/0006 700/250 |

FOREIGN PATENT DOCUMENTS

| | | |
|---|---|---|
| JP | 4426432 B2 | 3/2010 |
| KR | 10-1435514 B1 | 9/2014 |
| KR | 10-1438003 B1 | 9/2014 |
| KR | 10-1514467 B1 | 4/2015 |
| KR | 10-1517058 B1 | 5/2015 |

* cited by examiner

MOTION ASSISTANCE APPARATUS AND CONTROL METHOD OF THE SAME

CROSS-REFERENCE TO RELATED APPLICATION

This application claims priority under 35 U.S.C. § 119 to Korean Patent Application No. 10-2015-0125671, filed on Sep. 4, 2015, at the Korean Intellectual Property Office, the entire contents of which are incorporated herein by reference in their entirety.

BACKGROUND

1. Field

At least one example embodiment relates to a motion assistance apparatus and/or a control method of the motion assistance apparatus.

2. Description of the Related Art

With the onset of rapidly aging societies, many people may experience inconvenience and pain from joint problems, and interest in motion assistance apparatuses enabling the elderly, or patients with joint problems, to walk with less effort, may increase. Furthermore, motion assistance apparatuses for intensifying muscular strength of human bodies may be useful, e.g., for military purposes.

In general, motion assistance apparatuses for assisting motion of lower parts of human bodies may include body frames disposed on trunks of users, pelvic frames coupled to lower sides of the body frames to cover pelvises of the users, femoral frames disposed on thighs of the users, sural frames disposed on calves of the users, and pedial frames disposed on feet of the users. The pelvic frames and femoral frames may be connected rotatably by hip joint portions, the femoral frames and sural frames may be connected rotatably by knee joint portions, and the sural frames and pedial frames may be connected rotatably by ankle joint portions.

The motion assistance apparatuses may include active joint structures including hydraulic systems and driving motors to drive each joint portion to improve muscular strength of the legs of the users. For example, separate motors to transmit driving power may be provided at left and right hip joint portions, respectively.

SUMMARY

Some example embodiments relate to a motion assistance apparatus.

In some example embodiments, the apparatus may include a fixing module attached to a user, a driving module fixed to the fixing module to generate rotation power, a supporting module configured to support a portion of a body of the user and driven by the driving module, a force sensor configured to measure a magnitude of force applied to the fixing module, and a controller configured to adjust the rotation power of the driving module to minimize the magnitude of force measured by the force sensor.

The rotation power may include a driving torque used to drive the supporting module when the user wears the supporting module, and a compensation torque used to adjust the measured magnitude of force.

The controller may be configured to calculate a compensation torque such that the measured magnitude of force is equal to substantially zero (0), and apply the rotation power of the driving module by adding the calculated torque to the driving torque.

The fixing module may include a waist fixer configured to be in contact, for example in direct contact, with a waist of the user, a supporting frame configured to cover the waist fixer, and a joint configured to connect the waist fixer and the supporting frame.

The waist fixer may be formed of or include a flexible material, and the supporting frame may be formed of or include a rigid material.

The joint may be a universal joint including a multi-axis degree of freedom (DOF).

The force sensor may be disposed between the waist fixer and the waist of the user, or disposed between the waist fixer and the supporting frame.

An inertial measurement unit (IMU) sensor may be disposed on one side of the supporting frame to measure a waist movement of the user, and the IMU sensor may be configured to measure a degree to which the user bends at the waist and transmit the measured degree to the controller.

Other example embodiments relate to a control method of a motion assistance apparatus including a fixing module attached to a user, a driving module fixed to the fixing module to generate rotation power, a supporting module configured to support a portion of a body of the user and driven by the driving module, a force sensor configured to measure a magnitude of force applied to the fixing module, and a controller configured to control the driving module.

In some example embodiments, the method may include generating, by e.g., the driving module, a driving torque to drive the supporting module, measuring a direction and a magnitude of force indicated by the force sensor, calculating a compensation torque to minimize the measured magnitude of force, and driving the driving module by adding the compensation torque to the driving torque.

The fixing module may include a waist fixer configured to be in direct contact with a waist of the user and a supporting frame configured to cover the waist fixer, and measuring the magnitude of force indicated by the force sensor may include measuring a force acting between the waist fixer and the waist of the user.

Measuring the magnitude of force indicated by the force sensor may include measuring a force acting between the waist fixer and the supporting frame.

Measuring the direction of force indicated by the force sensor may include determining whether the direction of force increases a distance between the supporting frame and the waist of the user or decreases the distance between the supporting frame and the waist of the user.

Calculating the compensation torque may include increasing a compensation torque in a clockwise direction when the direction of force is determined to increase the distance between the supporting frame and the waist of the user.

Calculating the compensation torque may include increasing a compensation torque in a counterclockwise direction when the direction of force is determined to decrease the distance between the supporting frame and the waist of the user.

An IMU sensor may be disposed on one side of the supporting frame, and the method may further include measuring a waist movement of the user indicated by the IMU sensor.

The method may further include increasing a compensation torque in a clockwise direction when the user bends forward at the waist.

The method may further include increasing a compensation torque in a counterclockwise direction when the user bends backward at the waist.

The fixing module may include a first fixing module and a second fixing module fixed to both sides of the supporting frame, and calculating the compensation torque may include calculating a compensation torque applied to each of the first fixing module and the second fixing module separately.

The method may further include determining a compensation torque value as being equal to about zero (0) and driving the driving module using the driving torque when the measured magnitude of force is zero (0).

Additional example embodiments will be set forth in part in the description which follows and, in part, will be apparent from the description, or may be learned by practice of the example embodiments.

BRIEF DESCRIPTION OF THE DRAWINGS

These and/or other example embodiments will become apparent and more readily appreciated from the following description, taken in conjunction with the accompanying drawings of which.

DETAILED DESCRIPTION

Figure 1:
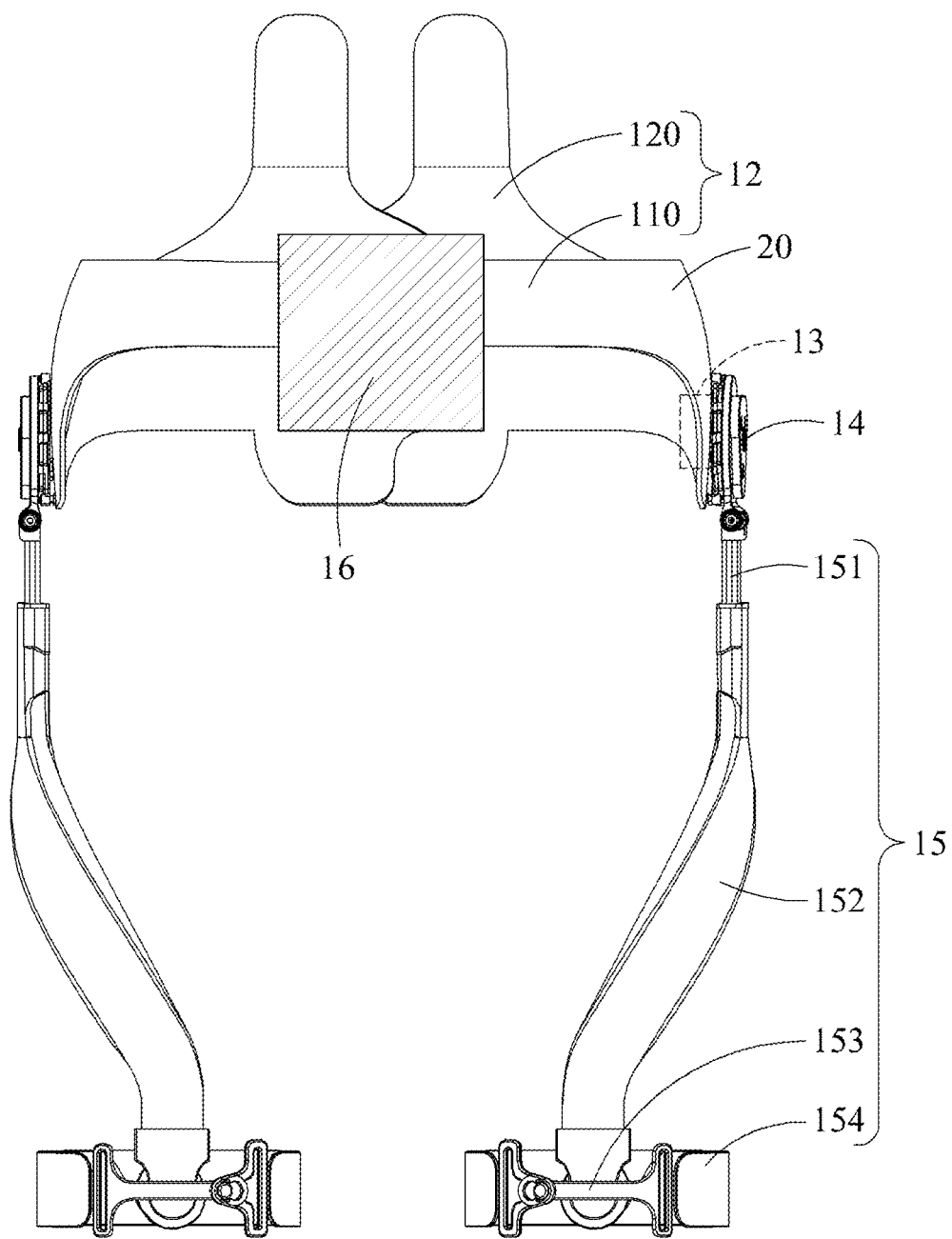
FIG. 1 is a front view illustrating a motion assistance apparatus, according to at least one example embodiment.

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of embodiments, detailed description of well-known related structures or functions will be omitted when it is deemed that such description will cause ambiguous interpretation of the example embodiments.

It should be understood, however, that there is no intent to limit the claimed invention to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It will be understood that when an element is referred to as being "on," "connected" or "coupled" to another element, it can be directly on, connected or coupled to the other element or intervening elements may be present. In contrast, when an element is referred to as being "directly on," "directly connected" or "directly coupled" to another element, there are no intervening elements present. As used herein the term "and/or" includes any and all combinations of one or more of the associated listed items. Further, it will be understood that when a layer is referred to as being "under" another layer, it can be directly under or one or more intervening layers may also be present. In addition, it will also be understood that when a layer is referred to as being "between" two layers, it can be the only layer between the two layers, or one or more intervening layers may also be present.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of example embodiments.

Various example embodiments will now be described more fully with reference to the accompanying drawings in which some example embodiments are shown. In the drawings, the thicknesses of layers and regions are exaggerated for clarity.

In the drawing figures, the dimensions of layers and regions may be exaggerated for clarity of illustration. Like reference numerals refer to like elements throughout. The same reference numbers indicate the same components throughout the specification.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, such as those defined in commonly-used dictionaries, should be interpreted as having a meaning that is consistent with their meaning in the context of the relevant art and will not be interpreted in an idealized or overly formal sense unless expressly so defined herein. As used herein, expressions such as "at least one of," when preceding a list of elements, modify the entire list of elements and do not modify the individual elements of the list.

When the terms "about" or "substantially" are used in this specification in connection with a numerical value, it is intended that the associated numerical value include a tolerance of ±10% around the stated numerical value. Moreover, when reference is made to percentages in this specification, it is intended that those percentages are based on weight, i.e., weight percentages. The expression "up to" includes amounts of zero to the expressed upper limit and all values therebetween. When ranges are specified, the range includes all values therebetween such as increments of 0.1%. Moreover, when the words "generally" and "substantially" are used in connection with geometric shapes, it is intended that precision of the geometric shape is not required but that latitude for the shape is within the scope of the disclosure. Although the tubular elements of the embodiments may be cylindrical, other tubular cross-sectional forms are contemplated, such as square, rectangular, oval, triangular and others.

Figure 2:
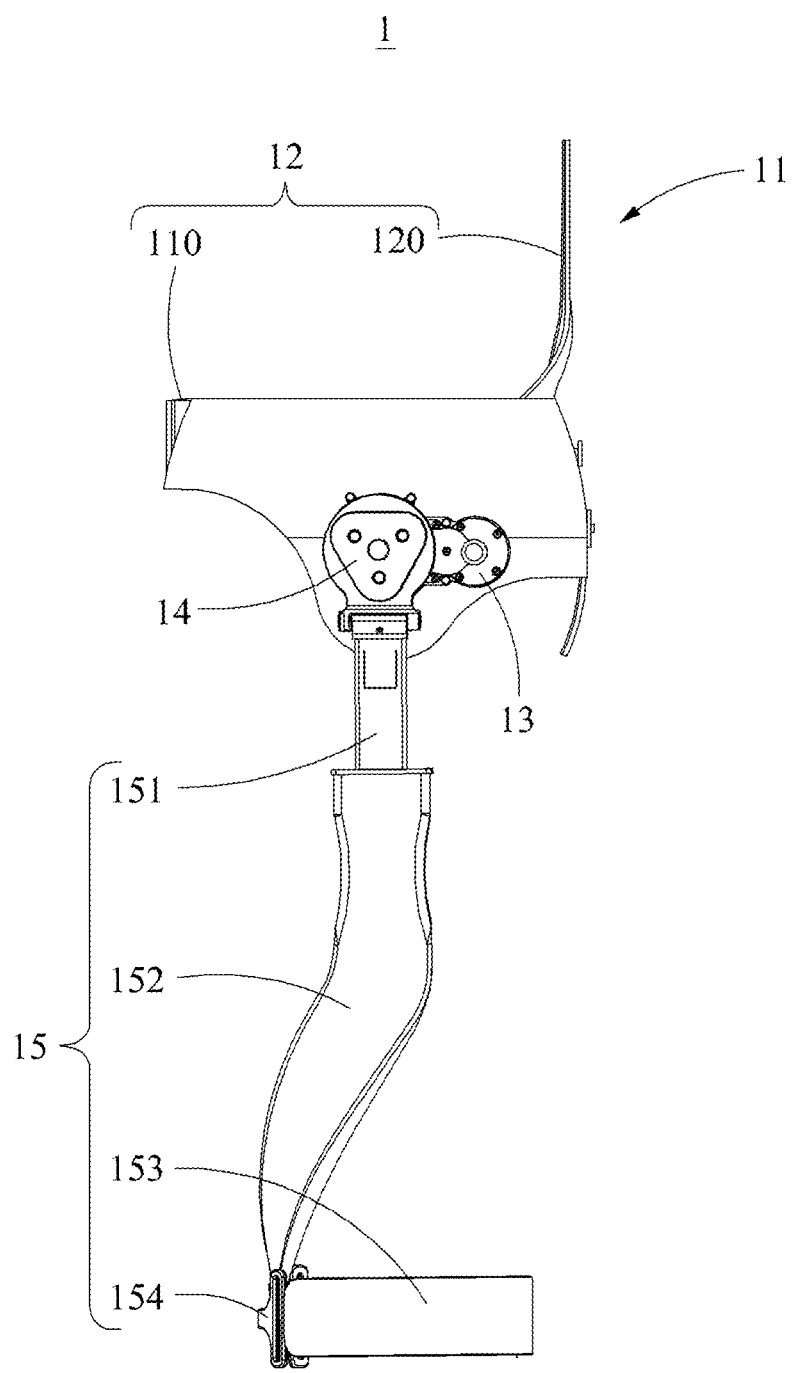
FIG. 2 is a side view illustrating a motion assistance apparatus, according to at least one example embodiment.

FIG. 1 is a front view illustrating a motion assistance apparatus 1, according to at least one example embodiment, and FIG. 2 is a side view illustrating the motion assistance apparatus 1, according to at least one example embodiment.

Referring to FIGS. 1 and 2, the motion assistance apparatus 1 may be worn by a user in order to assist a motion of the user.

The user may be a human, an animal, a robot or any other moving structure or being. However, example embodiments are not limited thereto. Further, although FIG. 1 illustrates a case in which the motion assistance apparatus 1 assists a motion of a thigh of the user, the motion assistance apparatus 1 may also assist a motion of another part of an upper body, for example, a hand, an upper arm, and a lower arm of the user, or a motion of another part of a lower body, for example, a foot, and a calf of the user. The motion assistance apparatus 1 may assist a motion of a part of the user. Hereinafter, a case in which the motion assistance apparatus 1 assists a motion of a thigh of a human will be described as an example.

The motion assistance apparatus 1 may include a fixing module 12, a driving module 13, a rotating joint 14, and a supporting module 15.

In example embodiments, the fixing module 12 may be attached to the user, and configured to cover an external surface of the user. For example, the fixing module 12 may be attached to one side of a waist of the user, and may include a curved surface corresponding to a contact portion of the user. The fixing module 12 may include a first side frame disposed on one side of the user, and a second side frame disposed on another side of the user. The first side frame and the second side frame may be provided to be attachable to and detachable from each other. A distance between the first side frame and the second side frame may be adjusted based on a body of the user.

The driving module 13 may provide power to be transmitted to the rotating joint 14. For example, the driving module 13 may be disposed in a lateral direction of the rotating joint 14, in detail, such that an axis of rotation of the driving module 13 may be spaced apart from an axis of rotation of the rotating joint 14. In this example, when compared to a case in which the driving module 13 and the rotating joint 14 share an axis of rotation, a height of a portion protruding from the user may relatively decrease. Unlike what the example drawings currently show, the driving module 13 may be spaced farther apart from the rotating joint 14. In this example, a power transmitting module may be additionally provided to transmit power from the driving module 13 to the rotating joint 14. The power transmitting module may be a rotary body such as, for example, a gear or the like, or a longitudinal member such as, for example, a wire, a cable, a string, a rubber band, a spring, a belt, a chain, and the like.

The rotating joint 14 may rotate by receiving power from the driving module 13. The rotating joint 14 may assist a motion of a joint portion of the user. The rotating joint 14 may be disposed on one side of the fixing module 12 at a position corresponding to the joint portion of the user. For example, the rotating joint 14 may be disposed on one side of a hip-joint of the user. One side of the rotating joint 14 may be connected to the driving module 13, and another side of the rotating joint 14 may be connected to the supporting module 15.

In example embodiments, the supporting module 15 may support a portion of the user, and may assist a motion of the portion of the user. The supporting module 15 configured to rotate using torque of the rotating joint 14 may include a hinge connection structure connected to the rotating joint 14. In this example, by a hinge axis of the hinge connection structure and a rotation axis of the rotating joint 14, the supporting module 15 may perform a two-degree of freedom (DOF) motion with respect to the fixing module 12. The supporting module 15 may include a sliding joint 151, a thigh frame 152, an applying member 153, and a supporting band 154.

The sliding joint 151 may connect the rotating joint 14 and the thigh frame 152, and may rotate using the torque of the rotating joint 14. The sliding joint 151 may be movably installed in the thigh frame 152.

The thigh frame 152 may transmit a force to a portion of the user. One end portion of the thigh frame 152 may be rotatably connected to the sliding joint 151, and another end portion of the thigh frame 152 may be connected to the supporting band 154 to transmit a force to a portion of the user. For example, the thigh frame 152 may push or pull the thigh of the user. The thigh frame 152 may extend and may bend in a longitudinal direction of the thigh of the user to cover at least a portion of the circumference of the thigh of the user. The one end portion of the thigh frame 152 may be disposed on a side surface of the thigh of the user, and the other end portion of the thigh frame 152 may be disposed on a front surface of the thigh of the user. A surface on the side of the one end portion of the thigh frame 152 may be substantially orthogonal to a surface on the side of the other end portion of the thigh frame 152.

In example embodiments, the applying member 153 may be connected to the other end portion of the thigh frame 152 to apply a force to a portion of the user. For example, the applying member 153 may be disposed along the front surface of the thigh of the user, or in a circumferential direction of the thigh of the user to push or pull the thigh of the user. The applying member 153 may include a curved surface corresponding to the thigh of the user and extending from the other end portion of the thigh frame 152 toward both sides of the thigh frame 152.

The supporting band 154 may be connected to one side of the applying member 153. For example, the supporting band 154 may be disposed to cover at least a partial circumference of the thigh of the user, thereby reducing or substantially preventing separation between the thigh of the user and the thigh frame 152.

Figure 3:
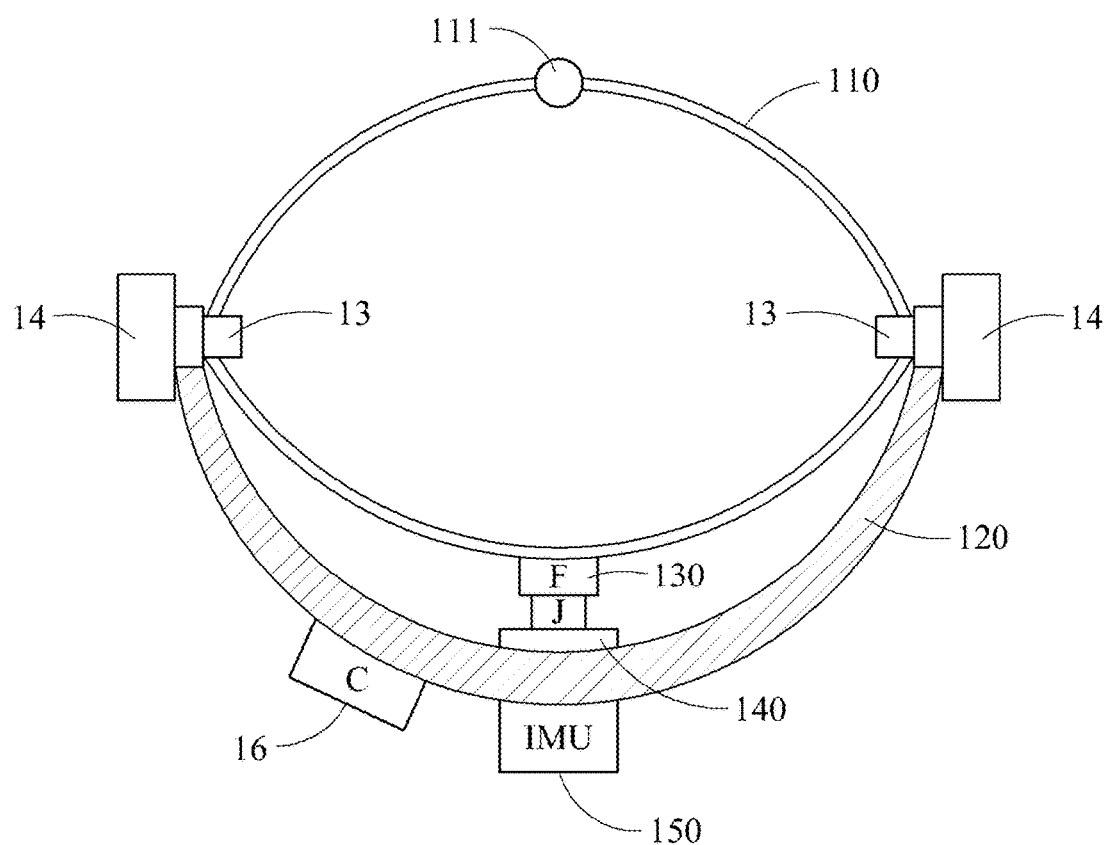
FIGS. 3 through 5 are top views illustrating a motion assistance apparatus, according to at least one example embodiment.
Figure 4:
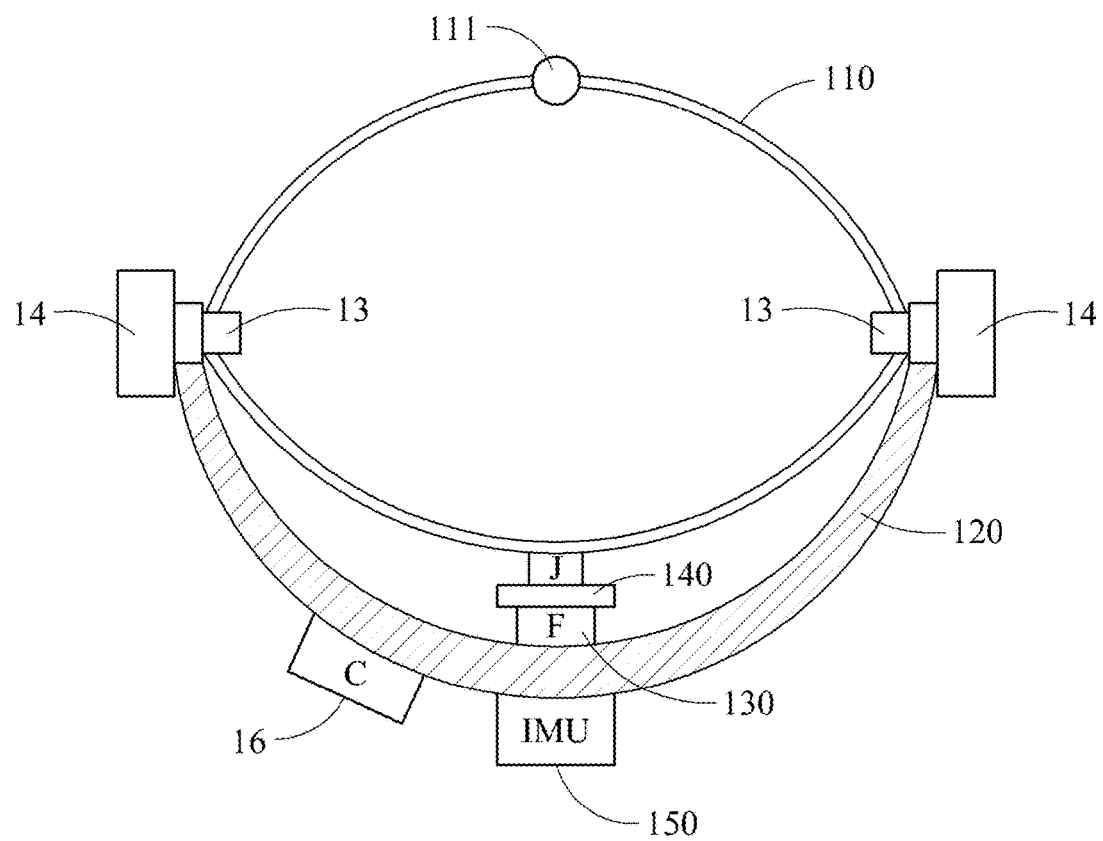
Figure 5:
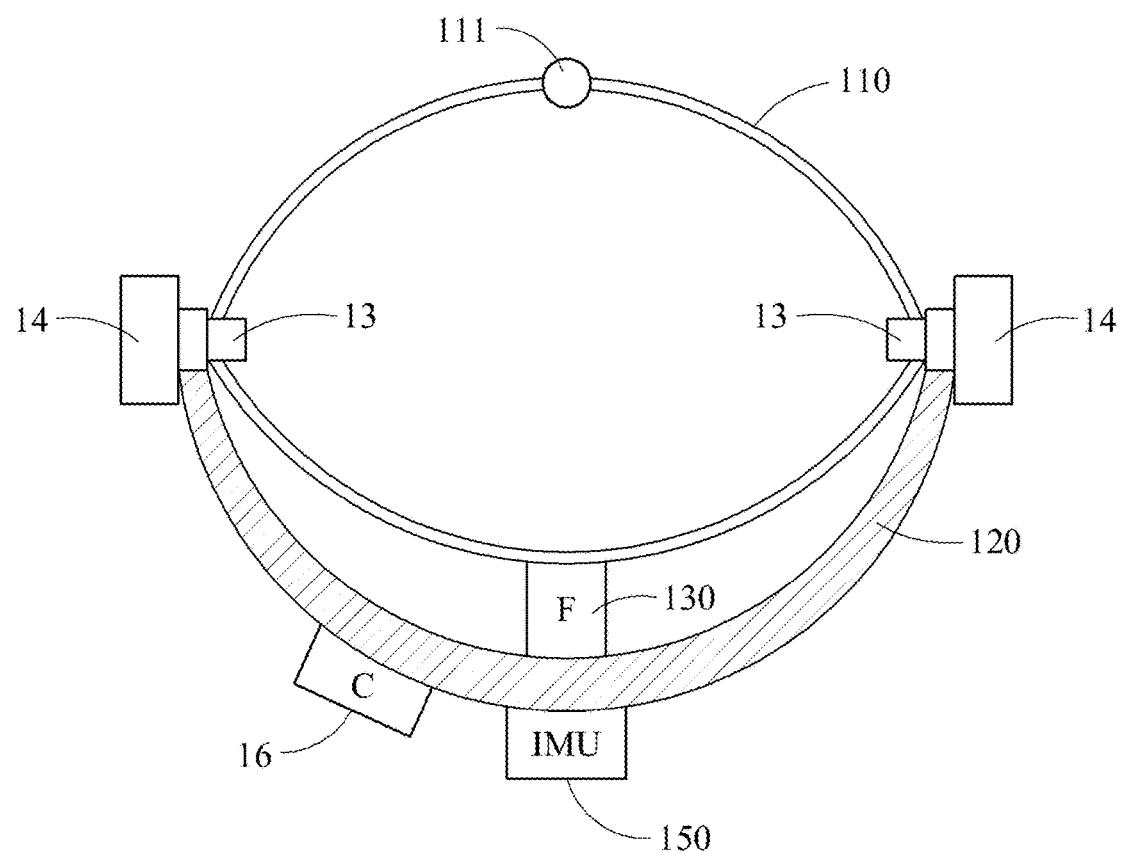

FIGS. 3 through 5 are cross-sections of the motion assistance apparatus 1, for example, cross-sections passing through a waist part of a user wearing the motion assistance apparatus 1.

In example embodiments, in the motion assistance apparatus 1, a force sensor 130 may be disposed in a portion of the fixing module 12 to measure a magnitude of the force applied to a waist of the user. Since the fixing module 12 and the user transmits and receives the same magnitude of force to and from each other by action and reaction, the force sensor 130 may measure the force applied by the user to the fixing module 12.

The force generated by the driving module 13 on the right side or the left side may be transferred to another driving module through supporting frame 120. The weight of the user applied to the motion assistance apparatus 1 by gravity, and the force generated by the driving module 13, may be transferred to the waist fixer 110 through the supporting frame 120, and the force sensor 130 may measure the force.

The fixing module 12 may include the waist fixer 110 configured to be in contact, for example in direct contact, with the waist of the user by covering the waist, the supporting frame 120 configured to cover an outer side of the waist fixer 110, and a joint 140 configured to connect the waist fixer 110 and the supporting frame 120.

The waist fixer 110 may be in close contact with the waist of the user, and may be formed of or include a fabric material to reduce or substantially prevent inconvenience to the user. The waist fixer 110 may include a Velcro member 111 at an abdominal part of the user, the length of which being adjustable by the user. The waist fixer 110 may fix the motion assistance apparatus 1 to a body and may reduce or substantially prevent separation of the motion assistance apparatus 1 from the body due to, for example, gravity.

The supporting frame 120 may cover the waist fixer 110, and may be formed of or include an inflexible and rigid material. To reduce weight, the supporting frame 120 may include a material of, for example, aluminum, titanium, and/or carbon fiber.

The supporting frame 120 may fully cover the waist fixer 110. Alternatively, the supporting frame 120 may be configured to cover a portion from a leg joint to an abdomen of the user. Since it may be relatively convenient for the user to wear the waist fixer 110 on the abdomen, the supporting frame 120 may be configured to cover a portion from a leg joint to a back of the user.

In example embodiments, the waist fixer 110 and the supporting frame 120 may be connected to each other using the rotating joint 14 on each of the right side and the left side. The driving module 13 may be disposed on an inner side of the rotating joint 14. Additionally, to enhance a connection between the waist fixer 110 and the supporting frame 120 and to reduce or substantially prevent the waist fixer 110 and the supporting frame 120 from moving separately, the joint 140 may be disposed between the waist fixer 110 and the supporting frame 120. The joint 140 may be, for example, a universal joint including a multi-axis degree of freedom (DOF).

The joint 140 may provide a DOF between the waist fixer 110 and the supporting frame 120. Based on the DOF, the supporting frame 120 may move the waist fixer 110 without applying force. When the supporting frame 120 is totally free, the supporting frame 120 may autonomously move using force supplied from an external source and thus, the joint 140 may need to provide restraints thereon.

As an example, the aforementioned elements may be arranged in order of the waist fixer 110, the force sensor 130, the joint 140, and the supporting frame 120 with reference to FIG. 3. As another example, the aforementioned elements may be arranged in order of the waist fixer 110, the joint 140, the force sensor 130, and the supporting frame 120 with reference to FIG. 4. In this example, the force sensor 130 may measure a force acting between the waist fixer 110 and the supporting frame 120.

As illustrated in FIG. 5, the force sensor 130 may be disposed between the waist fixer 110 and the supporting frame 120 while the joint 140 is not disposed therebetween. Since the waist fixer 110 formed of or include a flexible material has the DOF, the force sensor 130 may be disposed between the supporting frame 120 and the waist fixer 110 and may connect the supporting frame 120 and the waist fixer 110 substantially without need of the joint 140.

A general 6-axis force/torque sensor may be used as the force sensor 130. To measure the force in a desired, or alternatively predetermined direction, a strain gauge may be used for the waist fixer 110 formed of or include the flexible material. Also, by using a spring structure, the force applied to the fixing module 12 may be calculated based on a displacement of a spring.

A controller 16 may be attached to one side of the supporting frame 120 and receive the magnitude of force measured by the force sensor 130. The controller 16 may adjust the rotation power of the driving module 13 to reduce or minimize the measured magnitude of force.

The rotation power of the driving module 13 may include a driving torque for driving the supporting module 15 in a normal state and a compensation torque for adjusting the magnitude of force measured by the force sensor 130. The normal state may indicate, for example, a state in which the user standing straight on the ground takes a step.

The controller 16 may calculate the compensation torque such that the measured magnitude of force is substantially zero (0), and may add the calculated compensation torque to the driving torque. Through this, the controller 16 may apply the rotation power of the driving module.

In example embodiments, an inertial measurement unit (IMU) sensor 150 may be disposed on one side of the waist fixer 110 or on one side of the supporting frame 120 to measure a waist movement of the user. When the IMU sensor 150 is disposed on the waist fixer 110, the waist movement of the user may be determined incorrectly due to a curve of the waist fixer 110. Thus, the IMU sensor 150 may be instead disposed externally on an outer side of the supporting frame 120, in which case the data collected may be more accurate compared to when the sensor is disposed between the supporting frame 120 and the waist fixer 110.

The IMU sensor 150 may measure a degree to which the user bends at the waist and transmits the measured degree to the controller 16. The controller 16 may measure the degree to which the user bends at the waist by using the IMU sensor 150, thereby determining whether the user bends forward or backward at the waist.

Figure 6:
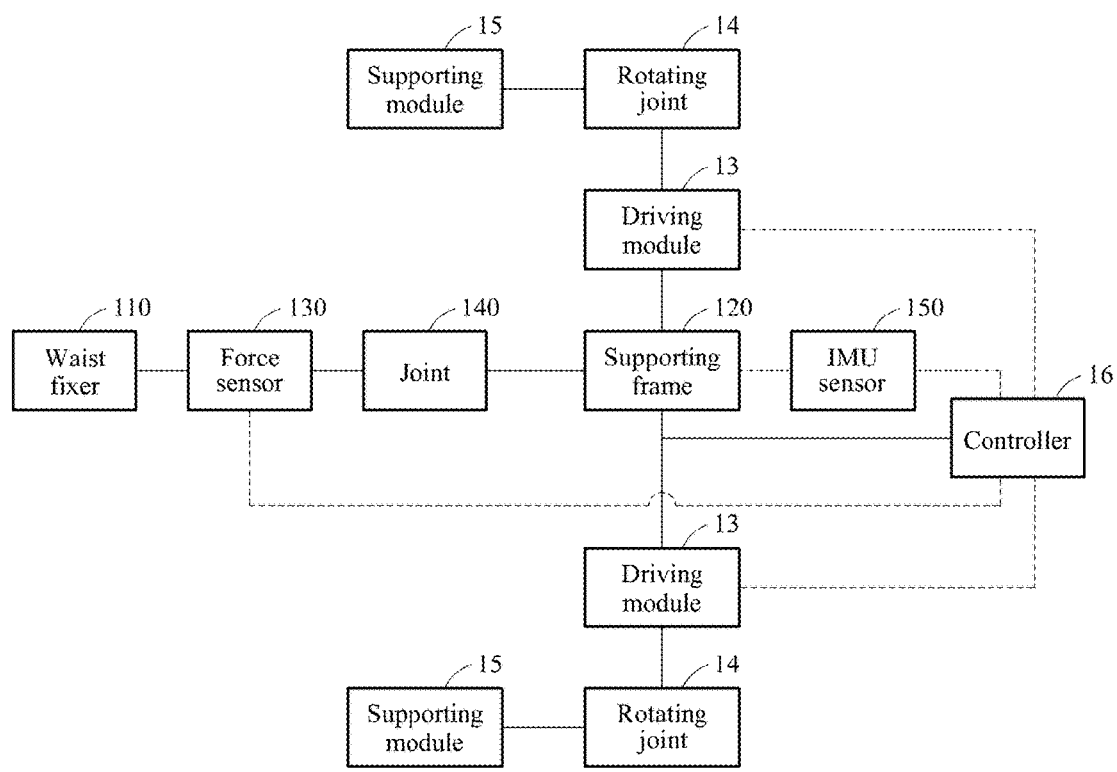
FIGS. 6 through 8 illustrate a configuration of a motion assistance apparatus, according to at least one example embodiment.
Figure 7:
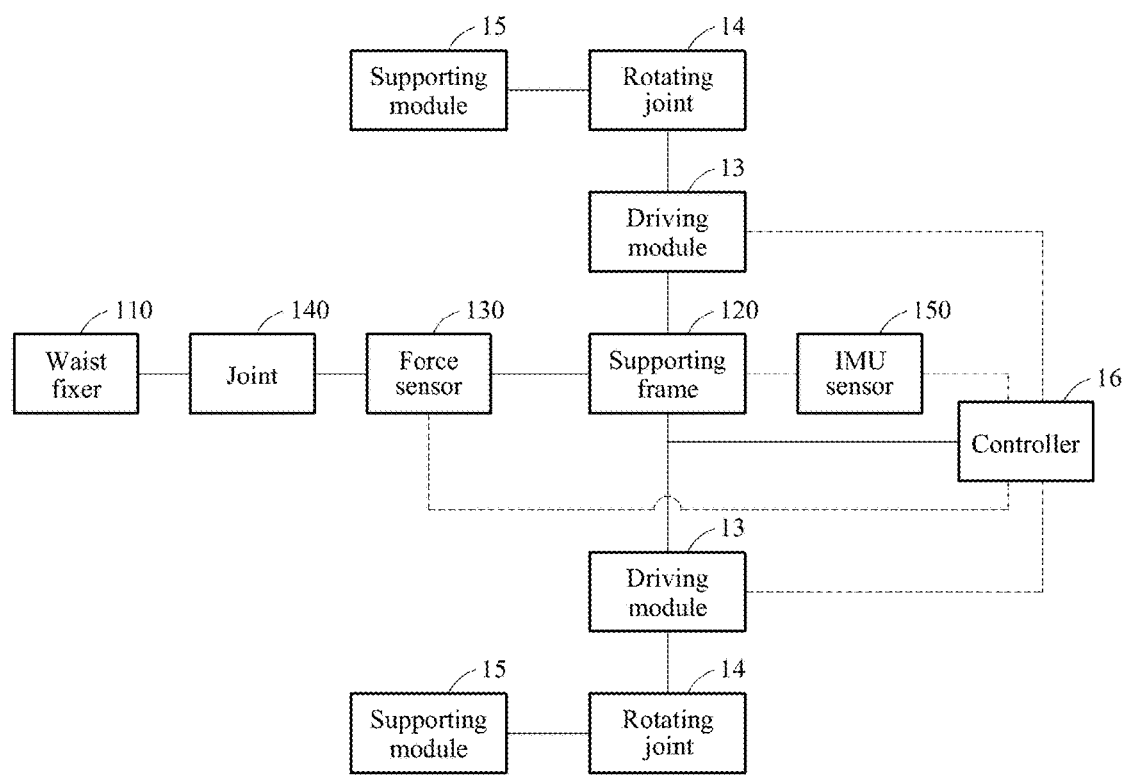
Figure 8:
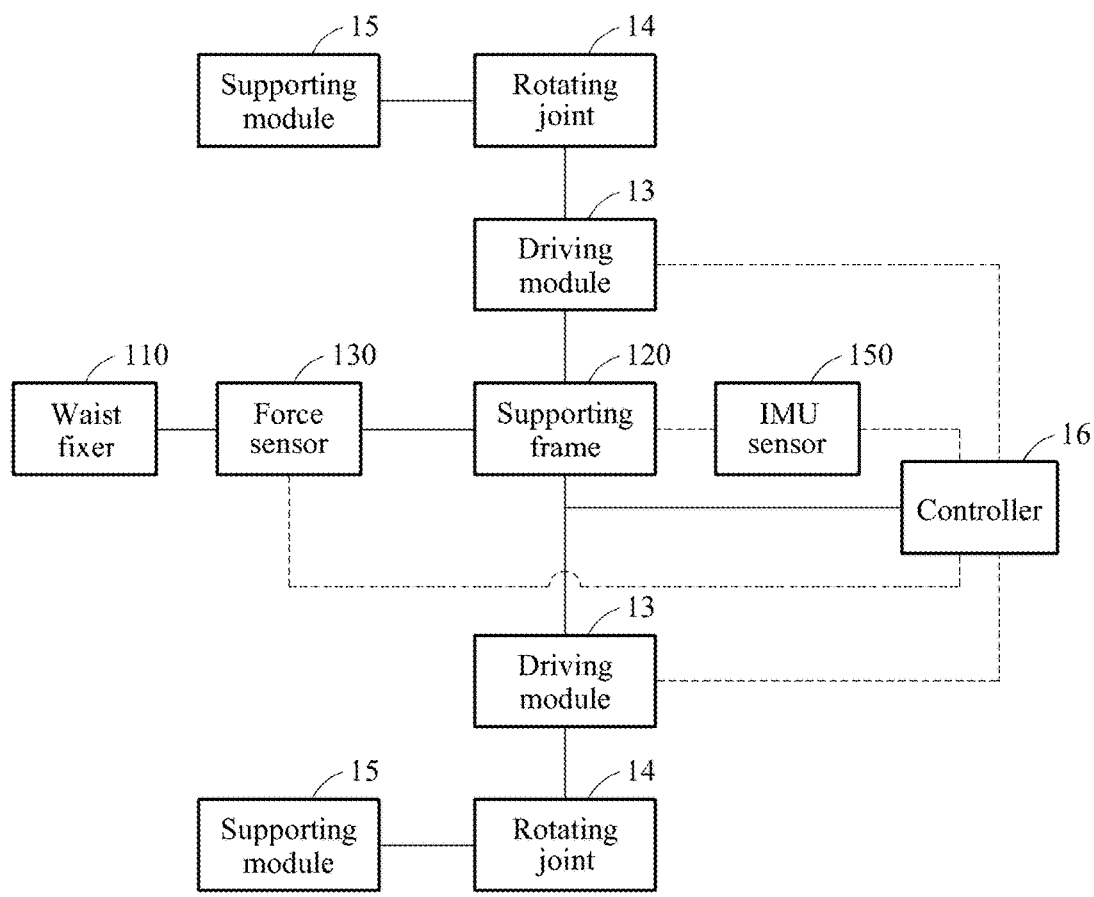

FIG. 6 illustrates an example configuration of the motion assistance apparatus 1 described with reference to FIG. 3. FIG. 7 illustrates an example configuration of the motion assistance apparatus 1 described with reference to FIG. 4. FIG. 8 illustrates an example configuration of the motion assistance apparatus 1 described with reference to FIG. 5. The configurations of FIGS. 6, 7, and 8 may have a difference in arrangement of the force sensor 130 and the joint 140.

In FIGS. 6 through 8, a physical and direct connection of elements may be indicated by a solid line. Also, an electric or wireless connection of elements may be indicated by a dashed line.

Figure 9:
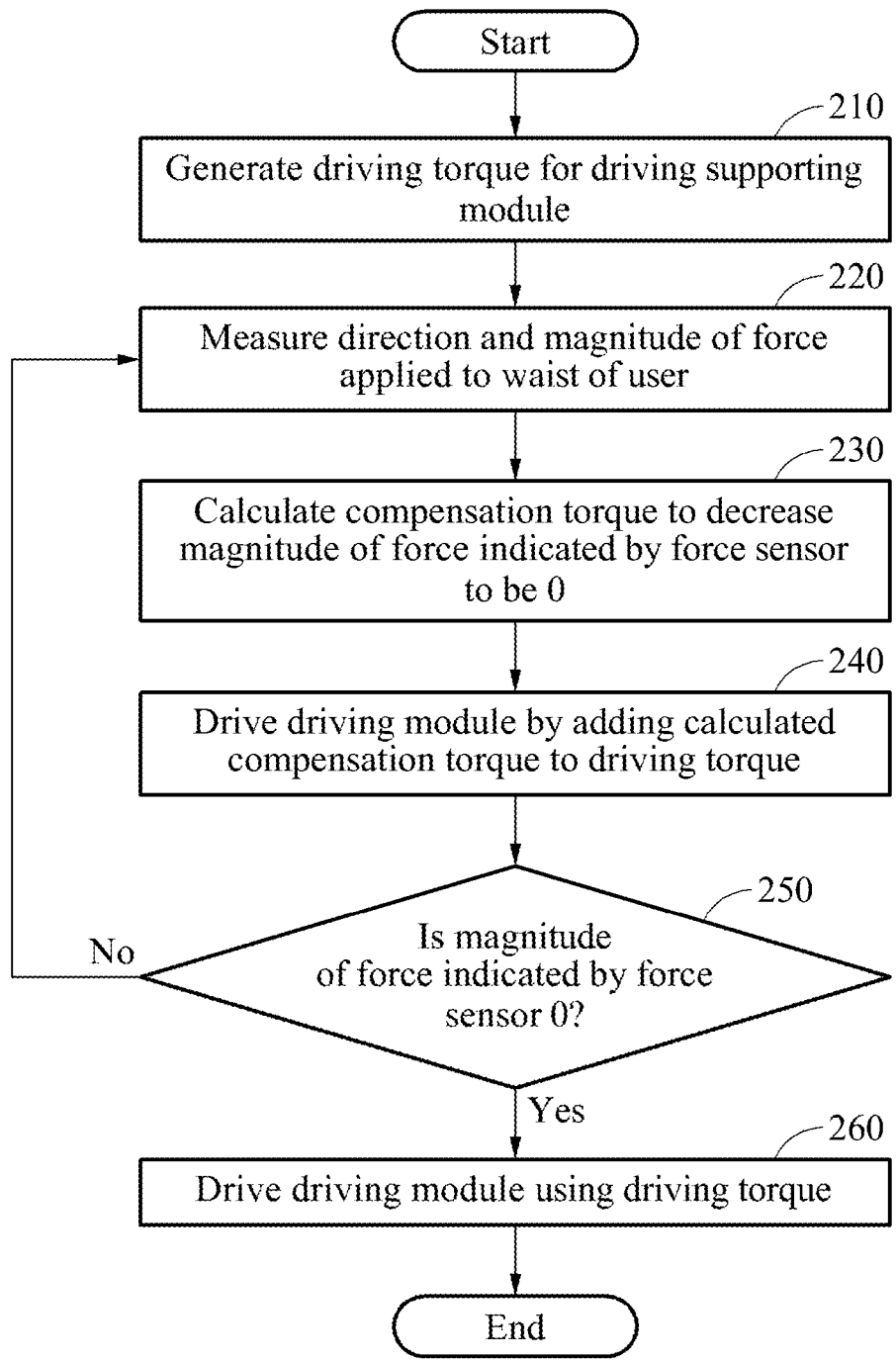
FIGS. 9 and 10 are flowcharts illustrating a control method of a motion assistance apparatus, according to at least one example embodiment.

FIG. 9 is a flowchart illustrating a control method of the motion assistance apparatus 1, for example, a compensation torque application scheme.

In FIG. 9, in operation 210, the driving module 13 may generate a driving torque for driving the supporting module 15. The driving torque may have a torque pattern and amplitude corresponding to the user. Also, the driving torque may be in a state in which a force applied by the fixing module 12 to a waist of the user is substantially equal to zero (0) while the user is standing upright and the waist is not bent in an environment not including a gradient.

In operation 220, the force sensor 130 may measure a direction and a magnitude of force applied to a waist of the user. The force sensor 130 may measure, for example, a force applied in a direction to a joint of the user, a force applied in a moving direction of the user, and a force applied in a reverse direction of the moving direction of the user.

The driving module 13 may be disposed in a relatively specific part of a joint between a leg and the waist of the user in order to rotate the supporting module 15. Thus, a magnitude of the force applied by the motion assistance apparatus 1 to the right joint portion or the left joint portion may be negligible except where the motion assistance apparatus 1 is twisted. In general, since a degree to which the waist moves leftward and rightward is less than a degree to which the waist moves forward and backward when the user walks, a force applied parallel with a gait direction may need to be measured accurately.

Based on a motion assistance apparatus provided in the structure described with reference to FIGS. 6 through 8, the force sensor 130 may measure the force applied between the waist fixer 110 and the supporting frame 120.

Also, the force sensor 130 may determine whether the direction of force increases or decreases a distance between the waist of the user and the supporting frame 120.

In operation 230, the controller 16 may calculate a compensation torque to decrease the magnitude of force indicated by the force sensor 130, for example, to be 0. Descriptions related to a method of calculating the compensation torque will be also provided with reference to FIG. 11.

When the direction of the force measured by the force sensor 130 is determined to increase the distance between the waist of the user and the supporting frame 120, the controller 16 may increase a compensation torque in a clockwise direction. Conversely, when the direction of force measured by the force sensor 130 is determined to decrease the distance between the waist of the user and the supporting frame 120, the controller 16 may increase a compensation torque in a counterclockwise direction.

As illustrated in FIGS. 6 through 8, the driving module 13 may include a first driving module and a second driving module fixed to both sides of the supporting frame 120 to allow the right leg and the left leg of the user to move. The controller 16 may calculate compensation torques applied to the first driving module and the second driving module separately.

In operation 240, the controller 16 may drive the driving module 13 by adding the calculated compensation torque to the driving torque. The controller 16 may perform a separate calculation by adding the compensation torque applied to each of the first driving module and the second driving module to a previously applied corresponding driving torque.

In operation 250, the controller 16 may verify whether the magnitude of force indicated by the force sensor 130 is equal to substantially 0. When the magnitude of force indicated by the force sensor 130 is not equal to substantially 0, the magnitude and the direction of force indicated by the force sensor 130 may be calculated once more by returning to operation 220.

In operation 260, when the magnitude of force indicated by the force sensor 130 is equal to substantially 0, the controller 16 may determine a compensation torque value to be equal to substantially 0 and drive the driving module 13 using the driving torque.

Figure 10:
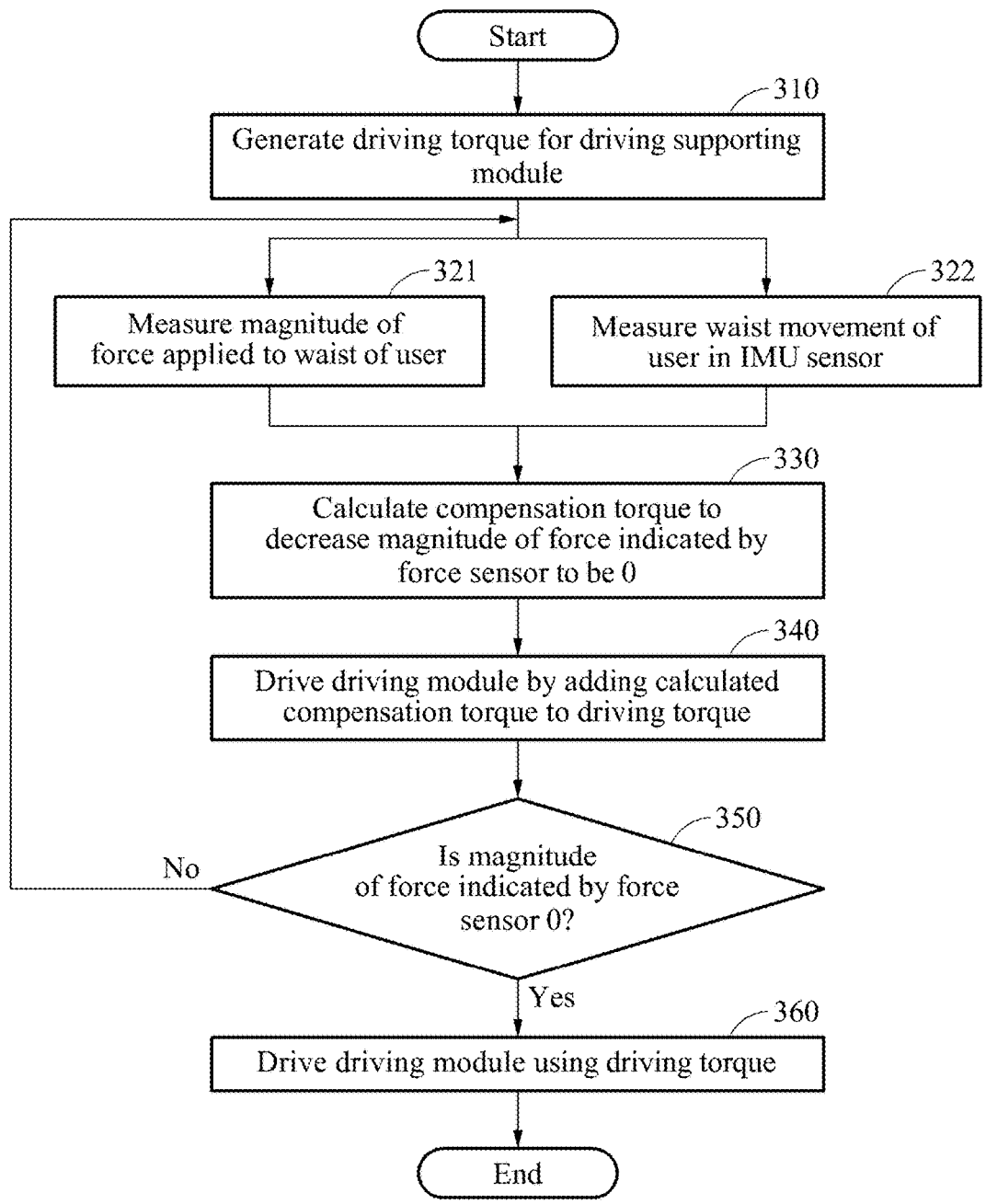

FIG. 10 is a flowchart illustrating a control method of a motion assistance apparatus configured to calculate a compensation torque using the force sensor 130 and the IMU sensor 150 simultaneously, in at least one example embodiment.

The IMU sensor 150 may be disposed on one side of the supporting frame 120 to measure a waist movement of a user. The IMU sensor 150 may be used selectively. The IMU sensor 150 may be used to add a pose control of the supporting frame 120 to constraints of an assistance torque calculation, thereby reducing an amount of assistance torque unnecessarily used due to a movement of the supporting frame 120.

In operation 310, the driving module 13 may generate a driving torque for driving the supporting module 15.

In operation 321, the force sensor 130 may measure a magnitude of force applied to a waist of the user. Simultaneously, the IMU sensor 150 may measure a waist movement of the user in operation 322. Operation 321 may be performed simultaneously with operation 322. Alternatively, operation 322 may be performed after operation 321.

In operation 330, the controller 16 may calculate a compensation torque to decrease the magnitude of force indicated by the force sensor 130, for example, to be equal to substantially 0. The compensation torque may be calculated by applying both the magnitude of force indicated by the force sensor 130 and the movement of the user indicated by the IMU sensor 150.

Figure 12A:
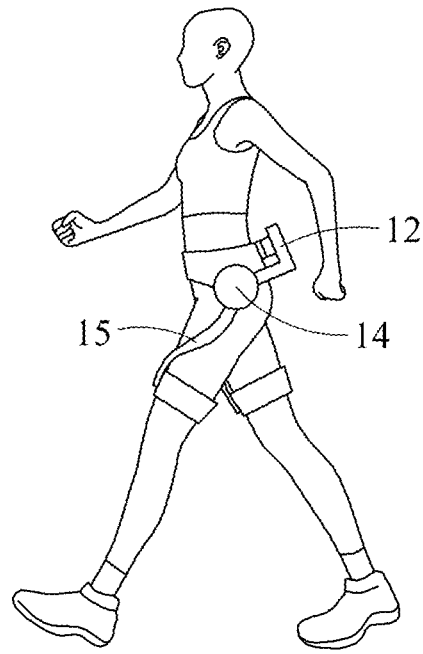
FIGS. 12A to 12C illustrate a movement of a user wearing a motion assistance apparatus, according to at least one example embodiment.
Figure 12B:
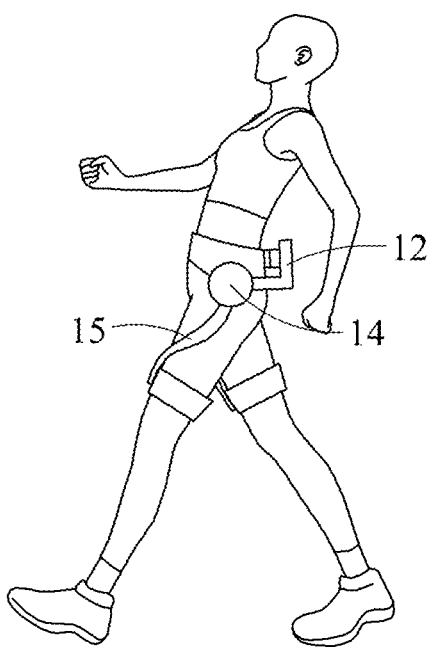
Figure 12C:
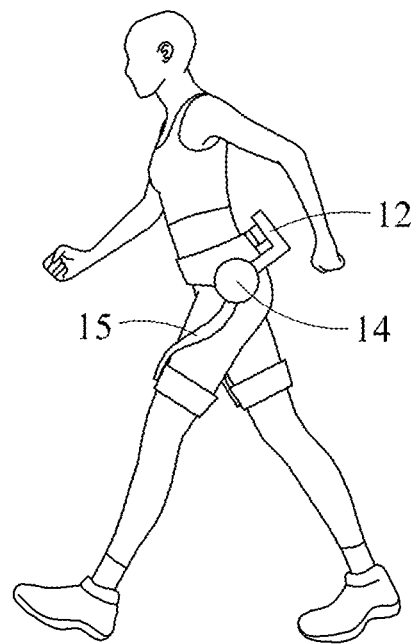

FIGS. 12A to 12C illustrate a movement of a user wearing the motion assistance apparatus 1, according to at least one example embodiment. The supporting module 15 may be mounted on a thigh of the user, the fixing module 12 may be attached to a waist of the user, and the rotating joint 14 may be disposed on a side of the fixing module 12.

FIG. 12A illustrates an example in which the user walks while keeping their waist straight. FIG. 12B illustrates an example in which the user walks while bending backward at the waist. FIG. 12C illustrates an example in which the user walks while bending forward at the waist.

As illustrated in FIG. 12B, when an IMU determines that the user bends backward at the waist, a force may be applied to decrease a distance between the waist of the user and the supporting frame 120 and thus, a compensation torque may increase in a counterclockwise direction.

As illustrated in FIG. 12C, when the IMU sensor determines that the user bends forward at the waist, the force may be applied to increase the distance between the waist of the user and the supporting frame 120 and thus, the compensation torque may increase in a clockwise direction.

In operation 240 of FIG. 9, the controller 16 may drive the driving module 13 by adding the calculated compensation torque to the driving torque. The controller 16 may perform a calculation by adding a compensation torque to be applied to each of a first driving module and a second driving module to a corresponding previously applied driving torque.

In operation 350 of FIG. 10, the controller 16 may verify whether the magnitude of force indicated by the force sensor 130 is equal to substantially 0. When the indicated magnitude of force is not equal to substantially 0, the control method may be performed by returning to operation 321 for calculating the magnitude and the direction of force indicated in the force sensor 130 and to operation 322 for measuring the waist movement of the user.

In operation 360, when the magnitude of force indicated by the force sensor 130 is equal to substantially 0, the controller 16 may determine a compensation torque value to be equal to substantially 0 and drive the driving module 13 using the driving torque.

Since a pose of the supporting frame 120 is to be measured by the IMU sensor 150 and the force acting between the waist fixer 110 and the supporting frame 120 is to be measured by the force sensor 130, the waist movement may be estimated using a model provided between the waist of the user and a waist fixer. When it is assumed that a mass of the waist is relatively large, a desired, or alternatively predetermined interval between the left side of the supporting frame and the right side of the supporting frame is maintained, and a change of direction, for example, in orientation, is free, the waist movement of the user may be calculated using a mass-motion-based dynamics model, for example, F=Mq+Cq+G.

Based on a gait pattern, for example, the phase of the user, a hip assist torque may be generated as a torque pattern of both legs before an assistance torque to be applied to each of the right leg and the left leg is calculated.

A torque pattern of the left driving module and the right driving module may be generated such that a desired force is indicated or the force measured by the force sensor 130 is minimized based on the hip assist torque.

A desired trajectory for a total force $F\_{total}$ to be applied to the user may be set as a constraint, and an assistance torque used generate a force $F\_{left}$ generated by the left driving module and a force $F\_{right}$ generated by the right driving module may be generated.

The total force $F\_{total}$ to be applied to the user may be a sum of the force $F\_{left}$ generated by the left driving module and the force $F\_{right}$ generated by the right driving module as shown below.

$$F\_{total} = F\_{left} + F\_{right}$$

To minimize the force transmitted to the waist fixer 110, the assistance torque may need to be generated such that the total force $F\_{total}$ is equal to substantially 0.

The desired trajectory for the total force $F\_{total}$ may be generated based on a gait strategy of the user, and the assistance torques to be applied to the left driving module and the right driving module may be generated within a range satisfying a targeted total force $F\_{total}(t)$.

For purposes of optimization, a cost function W may be set as shown below.

$$W = W1 * (F\_{total\_desired} - F\_{total\_measured}) + W2 * (desired\_assist\_torque - measured\_assist\_torque).$$

In addition to the setting, W1 and W2 may be adjusted to be suitable for the user, thereby optimizing the assistance torque and enhancing a wearability of a motion assistance apparatus.

Figure 11:
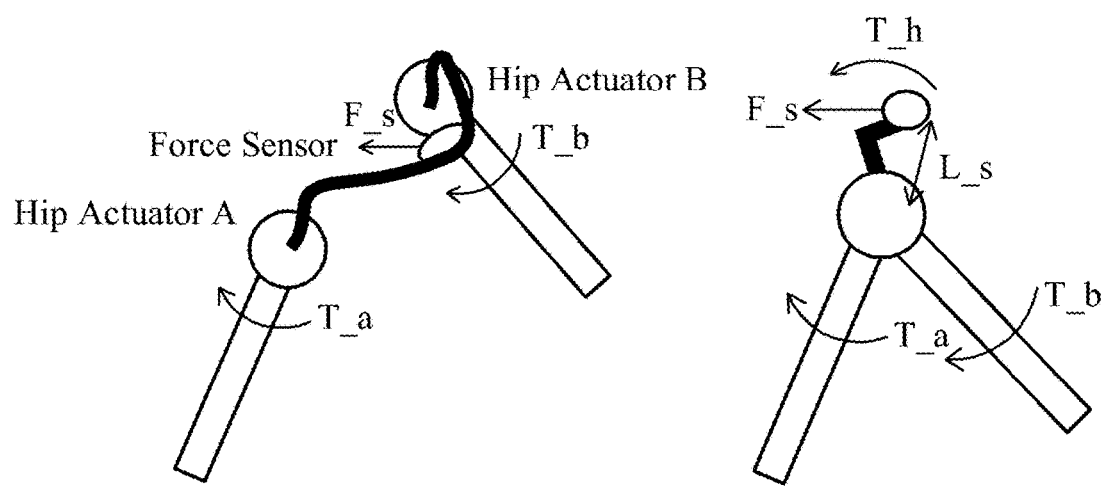
FIG. 11 illustrates an equation used in a control method of a motion assistance apparatus, according to at least one example embodiment.

Based on an example of FIG. 11, a method of calculating a compensation torque to implement the control method of a motion assistance apparatus illustrated in FIG. 9 will be explained with reference to the following descriptions.

In the following equations, e denotes error, d denotes a desired value, and m denotes a measured value.

$T\_a$ is a driving torque applied to a left driving module, and $T\_b$ indicates a driving torque applied to a right driving module. F-s is a magnitude of force measured by the force sensor 130, and L_s indicates a displacement distance between the rotating joint 14 and the force sensor 130.

In operation 220 of FIG. 9, a force applied to a waist may be measured based on Equation 1.

$$F\_{s,e} = F\_{s,d} - F\_{s,m} \quad \text{[Equation 1]}$$

In Equation 1, $F\_{s,d}$ denotes a desired magnitude of force, $F\_{s,m}$ denotes a measured magnitude of force, and $F\_{s,e}$ denotes a magnitude of force to be provided as a compensation.

Subsequently, in operation 220, the compensation torque may be calculated based on the following equations:

$$T\_{h,e} = F\_{s,e} * L\_s \quad \text{[Equation 2]}$$

In Equation 2, $T\_{h,e}$ indicates a value obtained by multiplying a distance between a sensor and a rotating joint to the magnitude of force to be provided as a compensation, the magnitude which is calculated in Equation 1.

$$T\_h = T\_{h,d} + T\_{h,e} \quad \text{[Equation 3]}$$

$T\_h$ denotes an actual torque applied to a driving module and may be obtained by adding $T\_{h,e}$ calculated in Equation 2 to the driving torque, $T\_{h,d}$.

$$(\text{Assist Torque}) T\_h = T\_a + T\_b \quad \text{[Equation 4]}$$

Based on the force error, $F\_{s,e}$, measured from the waist, an actual driving torque applied to the driving module to calculate an assistance torque may be modified from $T\_{h,d}$ to $T\_h$.

Output torques $T\_a$ and $T\_b$ of the left driving module and the right driving module may be determined based on the modified driving torque, $T\_h$ such that the driving module outputs $T\_h$ corresponding to a sum of $T\_a$ and $T\_h$ through a torque control in practice.

The units and/or modules described herein may be implemented using hardware components and software components. For example, the hardware components may include microphones, amplifiers, band-pass filters, audio to digital converters, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A motion assistance apparatus comprising:
   a fixing device including a waist fixer and a supporting frame, the waist fixer configured to be in direct contact with a waist of a user, and the supporting frame configured to cover the waist fixer;
   a driver fixed to the fixing device and configured to generate rotation power, the rotation power including at least two components, the two components being a driving torque and a compensation torque;
   a support configured to support a portion of a body of the user, the support being configured to be driven by the driver;
   a force sensor configured to measure a magnitude of a force acting between the waist fixer and the supporting frame, the force sensor being disposed on the fixing device; and
   a controller configured to determine a direction of the force acting between the waist fixer and the supporting frame based on data from at least the force sensor, and to determine whether the direction of the force increases a distance between the supporting frame and the waist fixer or decreases the distance between the supporting frame and the waist fixer, and to adjust the compensation torque to reduce the magnitude of the force measured by the force sensor.

2. The motion assistance apparatus of claim 1, wherein, the driving torque is associated with driving the support when the user wears the support, and
   the compensation torque is associated with adjusting the magnitude of the force.

3. The motion assistance apparatus of claim 2, wherein the controller is configured to,
   calculate the compensation torque such that the magnitude of the force is equal to substantially 0, and
   apply the rotation power of the driver by adding the compensation torque to the driving torque.

4. The motion assistance apparatus of claim 3, wherein the fixing device comprises:
   a joint configured to connect the waist fixer and the supporting frame.

5. The motion assistance apparatus of claim 4, wherein the waist fixer includes a flexible material and the supporting frame includes a rigid material.

6. The motion assistance apparatus of claim 4, wherein the joint comprises:
   a universal joint including a multi-axis degree of freedom (DOF).

7. The motion assistance apparatus of claim 4, wherein the force sensor is disposed between the waist fixer and the supporting frame.

8. The motion assistance apparatus of claim 4, further comprising:

an inertial measurement unit (IMU) sensor disposed on one side of the supporting frame, the IMU sensor is configured to, measure a degree of bending at the waist, and transmit the degree of bending to the controller.

9. A method of operating a motion assistance apparatus, the motion assistance apparatus including a fixing device attached to a body of a user, a driver fixed to the fixing device to generate rotation power, a support configured to support a portion of the body of the user and driven by the driver, a force sensor configured to measure a magnitude of force applied to the fixing device, and a controller configured to control the driver, the fixing device including a waist fixer and a supporting frame, the waist fixer configured to be in direct contact with a waist, and the supporting frame configured to cover the waist fixer, the force sensor being disposed on the fixing device, the method comprising:

generating, by the driver, a driving torque to drive the support;

measuring a direction and a magnitude of a force acting between the waist fixer and the supporting frame based on data from at least the force sensor;

determining whether the direction of the force increases a distance between the supporting frame and the waist fixer or decreases the distance between the supporting frame and the waist fixer;

calculating a compensation torque to reduce the magnitude of the force applied to the fixing device; and driving the driver by adding the compensation torque to the driving torque.

10. The method of claim 9, wherein the driving comprises:

increasing the compensation torque in a first direction when the direction of the force is determined to increase the distance between the supporting frame and the waist fixer.

11. The method of claim 10, wherein the driving comprises:

increasing the compensation torque in a second direction when the direction of the force is determined to decrease the distance between the supporting frame and the waist fixer, the second direction being an opposite direction as the first direction.

12. The method of claim 9, wherein an inertial measurement unit (IMU) sensor is disposed on one side of the supporting frame, and wherein the method further comprises:

measuring a waist movement indicated by the IMU sensor.

13. The method of claim 12, further comprising:

increasing the compensation torque in a first direction when there is forward bending at the waist.

14. The method of claim 13, further comprising:

increasing the compensation torque in a second direction when there is backward bending at the waist, the second direction being an opposite direction as the first direction.

15. The method of claim 9, wherein the driver includes a first driver and a second driver fixed to a first side and a second side of the supporting frame, respectively, and wherein the calculating comprises:

calculating the compensation torque applied to each of the first driver and the second driver separately.

16. The method of claim 9, further comprising:

determining whether a value of the compensation torque is substantially equal to 0; and driving the driver using the driving torque when the magnitude of the force is substantially equal to 0.

* * * * *